US006286957B1

(12) United States Patent
Livnat

(10) Patent No.: US 6,286,957 B1
(45) Date of Patent: *Sep. 11, 2001

(54) DEVICE FOR MEASURING THE PATIENT'S PUPILS LOCATIONS, AND SYSTEM AND METHOD UTILIZING THE SAME FOR ADJUSTING PROGRESSIVE LENSES FOR THE PATIENT'S SPECTACLES

(75) Inventor: Ami Livnat, Arad (IL)

(73) Assignee: PDA Advanced Optic Systems, Ltd., Rosh Ha'Avin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/441,996

(22) Filed: Nov. 18, 1999

Related U.S. Application Data

(63) Continuation-in-part of application No. PCT/IL98/00304, filed on Jun. 30, 1998.

(51) Int. Cl.[7] .................................................. A61B 3/10
(52) U.S. Cl. ............................................................. 351/204
(58) Field of Search ................................... 351/204, 209, 351/202, 211, 210, 233, 243, 178, 177, 169

(56) References Cited

U.S. PATENT DOCUMENTS

| 3,454,331 | | 7/1969 | Maitenaz . | |
|---|---|---|---|---|
| 4,167,067 | | 9/1979 | Guiset . | |
| 4,368,958 | | 1/1983 | Buget . | |
| 5,033,840 | * | 7/1991 | Hennequin et al. | 351/204 |
| 5,640,775 | | 6/1997 | Marshall . | |
| 5,691,799 | | 11/1997 | Ramachandran . | |
| 5,984,473 | * | 11/1999 | Livnat | 351/177 |

FOREIGN PATENT DOCUMENTS

| 2 384 232 | 10/1978 | (FR) . |
|---|---|---|
| 2 672 792 | 8/1992 | (FR) . |

* cited by examiner

Primary Examiner—George Manuel
(74) Attorney, Agent, or Firm—Browdy and Neimark

(57) ABSTRACT

A device is presented for determining patient's pupils locations in natural reading mode. The device includes a target member with a reading material on its outer surface, and a video camera mounted within the target member. The target member is orientable by the patient in a manner corresponding to his habitual reading position. The video camera is disposed such that the patients eyes are located within the depth of field of the camera, the camera thereby acquiring an image of the patients' eyes in a frame of his spectacles in his habitual reading position.

21 Claims, 8 Drawing Sheets (GENERAL ART)

(GENERAL ART)

(GENERAL ART)

(GENERAL ART)

DEVICE FOR MEASURING THE PATIENT'S PUPILS LOCATIONS, AND SYSTEM AND METHOD UTILIZING THE SAME FOR ADJUSTING PROGRESSIVE LENSES FOR THE PATIENT'S SPECTACLES

CROSS REFERENCE TO RELATED APPLICATION

The present application is continuation-in-part of International Application No. PCT/IL98/00304, filed Jun. 30, 1998, the entire contents of which being hereby incorporated herein by reference.

Said PCT application claims priority from U.S. application Ser. No. 08/887,327, filed Jul. 2, 1997, now U.S. Pat. No. 5,984,473.

FIELD OF THE INVENTION

The present invention relates to a method and a system for adjusting a pair of progressive lenses for mounting into the frame of a patient's spectacles, utilizing a device for measuring the patient's pupils locations relative to the frame in his natural habitual reading mode.

BACKGROUND OF THE INVENTION

Progressive lenses, also known as PAL (progressive addition lens), are widely used, especially by patients with weak eyesight in both reading and distance visions, like many presbyopes. There are different designs of progressive lenses produced by various manufacturers. As is known in the art, the two main features characterizing all designs of the progressive lens are optical power distribution and distortion distribution within the lens. FIGS. 1A and 1B illustrate two different examples, respectively, of these features for the same lens. There is practically no way of eliminating all the distortions.

The example of FIG. 1B presents a typical distortion map of a standard progressive lens. The lens has prescribed parameters of optical powers required for a patient's distance and reading visions and also cylinder parameters when necessary. The lens is formed with four main zones, wherein zone 2 is a far vision zone corresponding to the patient's distance vision, zone 3 is a near vision zone corresponding to the patient's reading vision, zones 5 are peripheral zones of concentrated optical distortion, defining a fourth zone 4 therebetween which is stretched between zones 2 and 3. This fourth zone 4 is a narrow passage, called "corridor", which is free of distortions and in which power varies continuously. All these features of the progressive lens are well known per se, and, therefore do not need to be described in detail, except to note that each standard semi finished PAL is characterized by its "addition" value (ADD), defined as the difference between the far and near vision powers.

The entire process conventionally carried out for providing a patient with PAL spectacles includes the following stages:

(1) determining for each eye values of the optical power required for the patient's reading and distance visions;

(2) selecting for each eye a semi finished lens of a suitable standard kind according to its "addition" value, and processing the inner side of the semi finished lens according to the prescribed values of the optical power and cylinder when necessary; and (3) cutting the lens, and mounting it in the frame of the spectacles (previously chosen by the patient) in such a position that the pupil location of the patient for far vision matches a Fitting Cross marking on the lens.

As illustrated in FIG. 2, the Fitting Cross 6A is a marking on the lens provided by the lens manufacture, and indicates the position of the far vision point that should be located in front of the patient's pupil center when looking at a far object. Generally, the only apparent relevant information about the lens supplied by the manufacturer to the optician is in the form of the following four standard stamped markings on the surface of the lens:

the Fitting Cross 6A which is the recommended position to mount the lens relative to the patient's pupil in distant vision;

a horseshoe marking 6B, which is the location recommended by the manufacturer for measuring the far vision power of the lens;

a Horizontal Fitting Line 7, which is the reference orientation line that should be horizontal when the lens is mounted in the frame; and a circle 8 is the center of the near vision zone, namely the location where the patient's line of sight is expected to pass when the patient reads.

In FIG. 2, numbers 9A and 9B designate "real" pupil locations (unmatched) for distance and reading vision, respectively, as found for a specific individual. The borders of the distortion zones 5 shown in dashed lines are typically unknown to the optician (concealed from view), and can only be detected by special instruments, mostly available to manufacturers, but still not to opticians. The location of the distortion zones 5 cannot practically be determined by the conventional equipment the optician has at his disposal.

Thus, by using the conventional techniques for adjusting lenses while mounting them into the spectacles' frame, the borders of the distortion zones 5 are not taken into consideration. Obviously, if while reading, the patient, for any reason, even slightly misses the recommended reading zone 8, his line of sight might pass through the highly distorted zone 5 and/or not at the appropriate power. This may result in blurred vision, eyestrains, focusing difficulty and itchy eyes. Reasons for missing the reading zone may be, for example, the result of erroneous fitting of the lens into the frame or, in other cases, when the patient holds the reading object (e.g., his book) too high or too low, or too far or too close from the position where the lens designer assumed it to be.

Although the rate of success in fitting progressives was appreciated to be relatively high according to past surveys, newly released independent surveys disclose that one out of three presbyopes is not satisfied with his PAL glasses. These unsatisfied patients use their progressive spectacles mainly for far sight and occasionally for near vision, but not for actual reading. For reading, they constantly turn to their usual reading glasses. The discrepancy between past and recent surveys is probably due to the fact that past surveys relied on the rate of progressives returned to the practitioners as a sole indicator. As it turned out, many unsatisfied customers for various reasons failed to return their unsuccessful progressives to their dispensers.

Apparently, one of the most significant rationale for the unsuccessful adaptation of a patient to his PAL glasses, is that the design of the PAL is performed according to statistical data. For example, it is well known that for most people, reading distance is about 35 cm, and, accordingly, the design of most progressives relies on this presumption. However, older individuals may, over time, develop different reading habits by positioning the reading material in various distances and angles relative to the body. This may have a devastating effect on the functioning of the progressive lens. The problem becomes even more complex, because for this age group, it is difficult, often painful, and sometimes even impossible, to change their reading habits.

Evidently, it is impractical to custom design a lens for every patient. On the other hand, very little can be done by the optician during the lens' mounting process, if he does not receive full and accurate information about the lens, as well as about his patient's habits. Moreover, even with enough information about the lens, the optician should be provided with means to apply a set of considerations and reasoning as to how many distortions and power errors should be allowed in order to ensure optimal fitting.

The typical procedure performed by the optician is illustrated in FIG. 3. The optician measures the far vision pupil's location relative to the selected frame independently for each lens, or alternatively derives this information from the measured inter pupillary distance. The respective data, as well as the spectacles' frame itself is input into a so-called "edger" device. The construction and operation of the edger are known per se, and therefore need not be specifically described, except to note that the edger is typically used for the circumferential cutting of a lens to fit the frame. Upon detecting that the pupil location for the distance vision overlaps the Fitting Cross 6A marked on the lens, the optician operates the edger for cutting the lens.

It is often the case that such a process of adjusting progressive lenses for a patient's spectacles renders unsatisfactory results, and many patients feel uncomfortable with their new spectacles for a long time. One of the reasons for this is that the adjustment is actually solely based on the distance vision parameters, while those of reading vision are completely ignored. This follows from the basic presumption that the patient, in the end, will adapt his reading habits to his lenses. Unfortunately, it seems that for a considerable number of patients, this never happens.

This limited success of PAL fitting was not unknown to those skilled in the art, and for many years efforts have been made to encourage "individual fitting", i.e., adapting the lens to the individual's parameters. Devices have been developed to provide the optician with more information concerning his patient and specifically, his pupils locations for near objects. Although various different approaches were utilized in developing these devices, yet they can generally be divided into three main groups.

Devices of the first and most popular group are known as "pupilmeters". These instruments deal exclusively with horizontal pupils decentration for near objects, and specifically for objects that are at a preset distance (usually 40 cm) from the patient's eyes. The object employed is a point light source that is translated, optically or physically, to this preset distance. The pupils' locations are measured mostly with good accuracy. However, these instruments cannot perform the measurement of an eye's drop. One of the latest models of this group, which is considered as the most advanced, is disclosed in U.S. Pat. No. 5,691,799. In distinction to other pupilmeters, this device is capable of measuring the pupils' horizontal decentration, while the patient wears his glasses. In other words, pupils locations are measured relative to the spectacles frame. However, the eyes' drops are still not measured. Since this device is stationary, rigidly mounted on a table with a patient's chin rest and head support, no reading can actually take place during measurement, and obviously not natural reading (i.e., in the natural reading position of the patient). Thus, although devices of the first group yield very accurate horizontal decentration results, the rate of success in fitting has not been meaningfully changed.

Devices of the second group do evaluate the eyes' drop. To this end, these devices utilize a point light source that is mounted somewhat lower than eye level. One of the devices of this kind is disclosed in U.S. Pat. No. 3,454,331. This device is positioned on a table (a "desktop model"), whereby the patient and optician sit at opposite sides of the table. The optician has an active role in operating the device by aligning it through a viewfinder (optical sight). The near object target is a point light source located a little higher than the table level, and the patient is asked to focus his eyes on the light source. During this procedure, the optician, through the viewfinder, aligns the device to capture the eyes' image with a conventional camera. This device advantageously measures a certain eye's drop. However, this measured eye's drop is a dictated one, and not necessarily the habitual reading eye's drop, because of its dependence on the table's height, the chair height and the patient's height. It works under the presumption that the patient will hold his book (or other reading material) on the table at a preset distance and angle. Additionally, the light source does not simulate a reading target, and the device cannot in any way be transformed to simulate natural reading, for example, by letting the patient hold the device in the most comfortable position and replacing the light source target by a reading target. Because of the optician's active role during measurement, it is impossible for the optician to stick his eye to the viewfinder while the device is held unsteadily by the patient.

The basic presumption of the above approach, which was also used in similar devices developed later, is that the patient's eyes' drop is not a personal parameter that should be learned and measured, but rather a controllable property. In other words, the patient is expected to adapt his eyes' drop to the given target, or at least be educated to do so whilst wearing his PALs. In view of the latest surveys, it seems that this approach is apparently inaccurate for a considerable number of presbyopes.

FR 2384232 discloses a simpler and improved version of the above device. This improved device is lightweight and has more convenient optical sight. However, it is still designed like a desktop-device, and cannot be transformed to a "handy" or "moveable" device, since it requires continuous alignment by the optician. FR 2672792 discloses an even more improved device, where optical sight is replaced with a camera. Similarly, it is designed like a desktop system with a light source target and a dictated reading angle. Deviation from this angle moves the patient's image out from the camera's field of view.

A different approach is utilized in systems of the third group. Such systems are disclosed, for example, in U.S. Pat. Nos. 4,368,958 and 5,640,775. Here, a device is mounted on the spectacle's frame, and the pupil's positions relative to the frame are measured. According to the technique of U.S. Pat. No. '958, the patient is asked to slide small opaque targets in front of his eyes until his viewing object, far or close, is obscured from view. The targets' positions, which represent his pupils' locations, are then measured. U.S. Pat. No. '775 discloses a similar approach, but here, the targets comprise small illuminated fiber optics. The targets appear as bright light spots in front of the patient's eyes. In distinction to U.S. Pat. No. '958, this device might utilize reading material. However, this device is unable to fulfill the basic conditions necessary to create a natural reading environment. Certainly, for many patients, it might be almost impossible to simulate their habitual reading while bright lights shine in front of their eyes.

SUMMARY OF THE INVENTION

There is accordingly a need in the art to substantially improve the conventional approach, by providing a novel device for measuring the patient's pupils' locations for reading, and a method and system using the same for adapting a prescribed progressive lens to a patient's eye by adjusting the lens for mounting into the frame of the patient's spectacles.

It is an object of the present invention to provide such a device that is capable of determining the patient's pupils' locations for his reading vision relative to the frame of the spectacles and specifically in his habitual reading position.

It is a further object of the present invention to provide such a method and system that would enable utilizing as much as possible information about the selected lens and the patient's eyesight, and to thereby adjust the lens to the patient's spectacles frame, or to replace the selected lens by another corrective one.

Thus, the main idea of the present invention is based on the fact that the near vision zone, in distinction to the far vision zone, is always surrounded by the distortion region, and therefore even slight missing of the pupil location from the prescribed region will significantly affect the patient's reading. Therefore, according to the present invention, a novel measurement device is used for measuring the patient's pupil locations in his habitual reading mode. This enables to provide optimal positioning of the progressive lens relative to the spectacles' frame.

The term "pupil location" used herein signifies the point of intersection of a line of sight with the frame plane. The term "optimal positioning" of the progressive lens signifies a positioning of the lens relative to the frame, such that it enables to provide a relative position of the lens at which pupils locations fulfill certain predefined tolerances relating to the power and distortion of the close and far neighborhoods of these locations.

There is thus provided, according to one aspect of the present invention, a device for determining patient's pupil locations for reading, the device comprising:

(a) a target member with reading material on its outer surface, wherein said target member is orientable by the patient in a manner corresponding to his natural reading position; and (b) a video camera mounted within said target member and disposed such that the patient's eyes are located within the depth of field of the camera, while said reading material is located out of the camera's depth of field, the camera thereby acquiring an image of the patients' eyes in a frame of his spectacles, whilst the patient reads said reading material in his natural reading position, enabling to determine an intersection of a line of sight of each patient's eye with a plane defined by the frame relative to the frame.

The camera may be used to acquire an image of a side view of the patient's face with the frame of the spectacles thereon, and/or may be displaceable to acquire an image of the pupils of the patient's eyes in the frame when disposed for distance vision. Alternatively, the device may comprises an additional camera for acquiring images of the side view of the patient's face and/or of the pupils of the patient's eyes in the frame when disposed for distance vision.

As indicated above, the optician, who has to adjust the pair of lenses supplied by the manufacturer to the spectacles frame selected by the patient, or to replace at least one of these lenses by a different one, should preferably be provided with full lens information (i.e., regarding power and distortion distributions in the lens) of all the different available lenses, preferably in the form of power and distortion maps. Lenses with different ADD should be considered as different lenses. Thus, the optician, having data indicative of the patient's true (natural) pupils locations relative to the chosen frame, in both distance and reading modes, specifically in his patient's habitual reading mode, will also have the power and distortion maps of all semi finished lenses that he may use. Moreover, the optician should be provided with a processor that will be able to analyze every pupil location relative to every lens' maps.

This analysis is based on the following factors: the "power error" at this location (i.e., the difference between the actual power at this location and the patient's prescribed power), the distortion value, and the latitudinal distortion symmetry. Turning back to FIG. 2, the "distortion symmetry" term can readily be clarified. It can easily be seen that although the pupil location 9B for reading vision lies in a distortion free zone, the latitudinal symmetry is pretty low. Indeed, moving the eye in a temporal direction will immediately bring the line of sight into the high distortion zone, while in the nasal direction, the distortion free zone is quite larger. Without elaborating, it is clear that a similar situation may occur for the distance vision location 9A, especially in case of lens rotation. The analysis should also include the evaluation of the difference between the line connecting the two pupil locations 9A and 9B (FIG. 2), and the original line of continuous focal change which connect the Fitting Cross 6A with the center of marking 8. This evaluation should be carried out by comparing the powers and distortion values point by point between and along these two lines. Obviously, the analysis is not limited to the above indicated four parameters, and other or additional parameters can also be considered.

Essentially, all of the conventional matching-aimed methods presume a priori that such matching does actually exist, i.e. that by appropriate translations (but absolutely not rotations), or alternatively, by the suitable selection of a lens from different brands, correct matching can be reached. None of the prior art methods actually dealt with cases where absolute matching could not be achieved. It is generally agreed that this case goes beyond the ability of the optician or the fitting process. It is hoped that the patient eventually gets used to his new PAL by changing, for example, his reading habits in favor of reading through the recommended Reading Circle mark. Unfortunately, it was found that for many older individuals this is a hard and painful process, and sometimes even impossible to accomplish.

The method of the present invention, contrary to the prior art techniques, ignores the manufacturer's markings, which depend only on a few of the lens' parameters, but rather makes use of the lens' power and distortion maps. By employing a programmed processor, it utilizes not only the power and distortion of the exact pupil location, but also relates to close and far neighbors of this location. By performing translations and/or rotations and/or selection of different ADD (not excluding the selection of a different brand if available), the method of the present invention is aimed at attaining optimal fitting, even though perfect matching cannot be achieved. According to the method of the present invention, the matching process extends beyond the stage, where no matching to lens' markings can actually be achieved.

Thus, in accordance with another aspect of the invention, there is provided a method for adjusting a progressive lens relative to the frame of a patient's spectacles, wherein the lens has power and distortion distributions defining far and near vision zones which are located in accordance with prescribed first and second values of the optical power required for the patient's eye at its distance and reading modes, respectively, and are spaced from each other by a zone of continuously variable power, the method comprising the steps of:

(i) determining a location of intersection of a line of sight of the patient's eye at natural reading mode with a plane defined by the frame of the spectacles relative to said frame, wherein said determining is performed at the patient's habitual reading position by using a device comprising:

a target member having a reading material on its outer surface, wherein said target member is orientable by the patient in a manner corresponding to his habitual reading position; and a video camera mounted within said target member and disposed such that the patient's eyes are located within the depth of field of the camera, the camera thereby acquiring an image of the patients' eyes in a frame of his spectacles, whilst the patient reads said reading material in his natural reading position, enabling to determine the intersection of the line of sight of each patient's eye with the plane defined by the frame relative to the frame;

(ii) determining the distributions of said optical power and optical distortions of the progressive lens;

(iii) analyzing data indicative of the determined location of intersection of the line of sight of the patient's eye at said reading mode with the plane defined by the frame of the spectacles relative to said frame, and data indicative of the determined distributions of said optical power and optical distortions of the progressive lens, for determining whether an optimal positioning of the lens via at least one of a horizontal translation, a vertical translation, and a rotation of the lens relative to said frame can be achieved;

(iv) if said optimal positioning of the lens cannot be achieved, replacing the prescribed lens by another lens having at least one different parameter as compared to that of said prescribed lens; and (v) if said optimal positioning of the prescribed lens can be achieved, generating data representative thereof and using said generated data for mounting the lens into the frame For example, optimal positioning can be performed by evaluating the following properties: power error at the pupil location, distortion value, latitudinal symmetry for both far and near vision and deviation from the line of continuous power change connecting the Fitting Cross with the center of the Reading Circle.

The distributions of the optical power and of the optical distortions of the progressive lens may be determined by processing the lens in a so-called "mapping" system. The mapping system may be of any known kind, for example that commercially available from Rotlex Ltd. The device for positioning the lens may be a known "edger" device.

Alternatively or additionally, the distributions of the optical power and of the optical distortions of the progressive lens may be determined by analyzing reference data representative of a plurality of maps of standard lenses manufactured by various producers. This reference data is stored in the memory of a processor. In this case, the processor analyzes all the available lenses in the maps' storage, and relates them to the determined pupil locations of the patient. The analysis of the above data includes considerations of all possible rotations and translations for every lens. By summing up all the weights for every practical option, the processor can "recommend" the optimal fitting of the lens, i.e., the most compatible lens with the most recommended position relative to the frame.

If replacement of the selected lens by a different one is required, this different lens may have a different addition as compared to that of the selected lens, different power and distortion distributions, for example, with a broader or longer corridor. The positioning of the progressive lens relative to the frame might be performed with an edger device, in which linear and rotational movements of the lens are provided.

Preferably, the method also comprises the steps of determining a location of intersection of a line of sight of the patient's eye at distance mode with a plane defined by the frame of the spectacles relative to said frame.

According to yet another aspect of the present invention, there is provided a system for adjusting a progressive lens relative to a frame of a patient's spectacles, wherein the lens has distributions of the optical power and optical distortions therein defining far and near vision zones which are located in accordance with prescribed first and second values of the optical power required for the patient's eye at its distance and reading modes, respectively, and are spaced from each other by a zone of continuously variable power, the system comprising:

a device for determining a location of intersection of a line of sight of the patient's eye for the natural reading mode with a plane defined by the frame of the spectacles relative to said frame, wherein said device comprises:

a target member having a reading material on its outer surface, wherein said target member is orientable by the patient in a manner corresponding to his natural reading position; and a video camera mounted within said target member and disposed such that the patient's eyes are located within the depth of field of the camera, the camera thereby acquiring an image of the patients' eyes in a frame of his spectacles, whilst the patient reads said reading material in his natural reading position, enabling to determine the intersection of the line of sight of each patient's eye with the plane defined by the frame relative to the frame;

a device for determining the distributions of said optical power and said optical distortions of said progressive lens;

a processor capable of analyzing data indicative of the determined location of the intersection of the line of sight of the patient's eye at said natural reading mode with the plane defined by the frame of the spectacles relative to said frame, and data indicative of the determined distributions of said optical power and optical distortions of the progressive lens, and generating data indicative of an optimal positioning of the lens relative to said frame; and a device for positioning said progressive lens via at least one of a horizontal translation, a vertical translation, and a rotation relative to said frame for mounting the lens into the frame at said optimal position of the lens.

BRIEF DESCRIPTION OF THE DRAWINGS

In order to understand the invention and to see how the same may be carried out in practice, a preferred embodiment will now be described, by way of example only, with reference to the accompanying drawings, in which.

DETAILED DESCRIPTION OF THE PREFERRED EMBODIMENTS

Figure 1A:
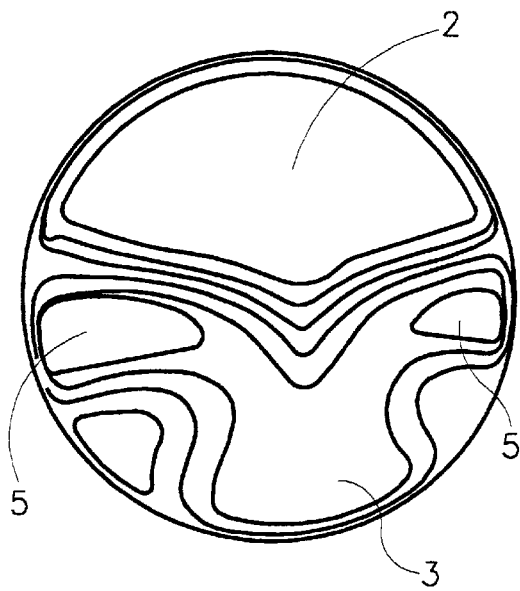
FIGS. 1a and 1b are two examples, respectively, of power and distortion distributions in a conventional progressive addition lens (PAL)
Figure 1B:
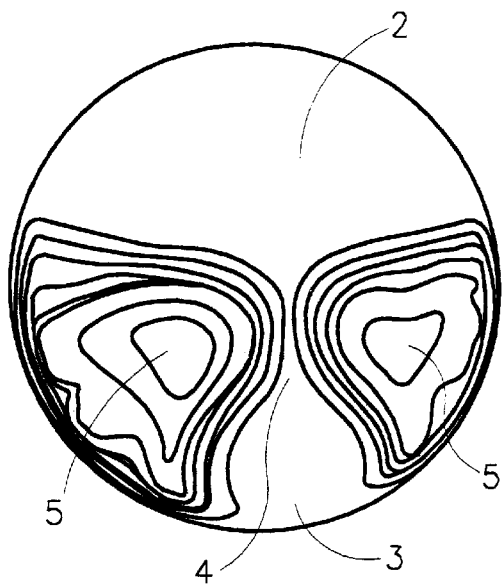
Figure 2:
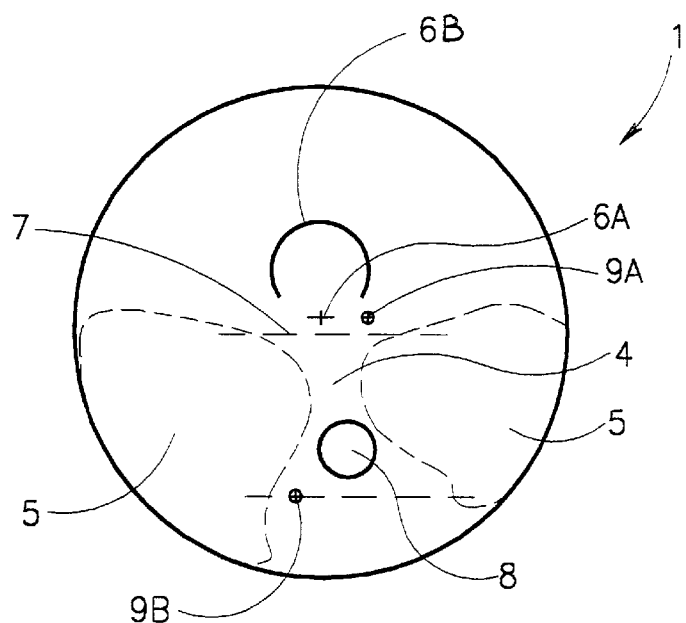
FIG. 2 shows the main parameters of the lens as conventionally supplied to an optician and several lens parameters that can and cannot be determined by the optician with the conventional techniques.
Figure 3:
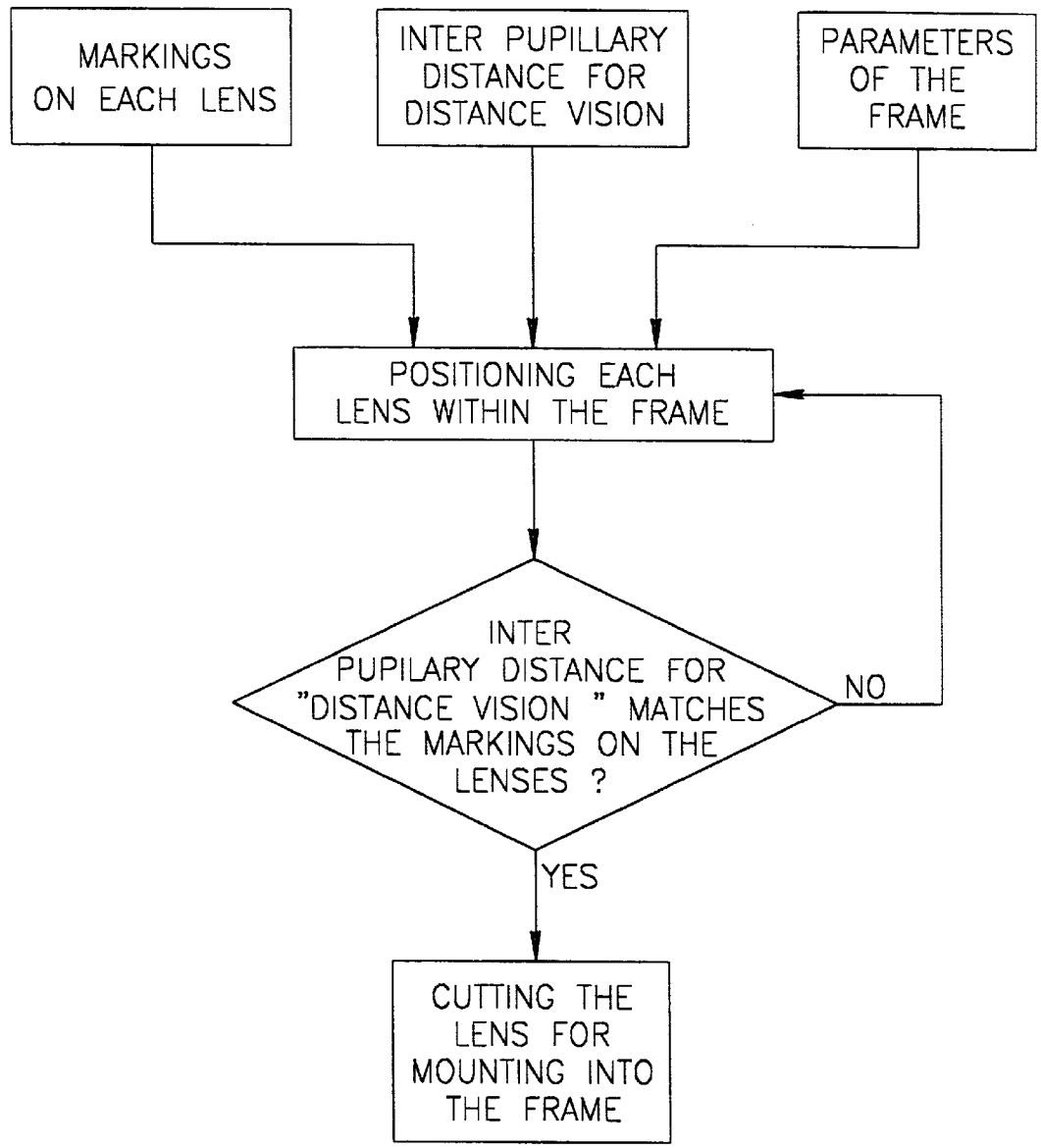
FIG. 3 is a flow diagram illustrating the principles of the conventional technique used by an optician for adjusting a pair of prescribed progressive lenses for mounting into the frame of a patient's spectacles.

FIGS. 1a, 1b and 2 illustrate the main characteristics of a conventional progressive lens of the kind to which the present invention refers. FIG. 3 illustrates the main steps of a conventional process of adjusting a lens such as shown in FIG. 2 for mounting in the frame of a patient's spectacles.

Figure 4:
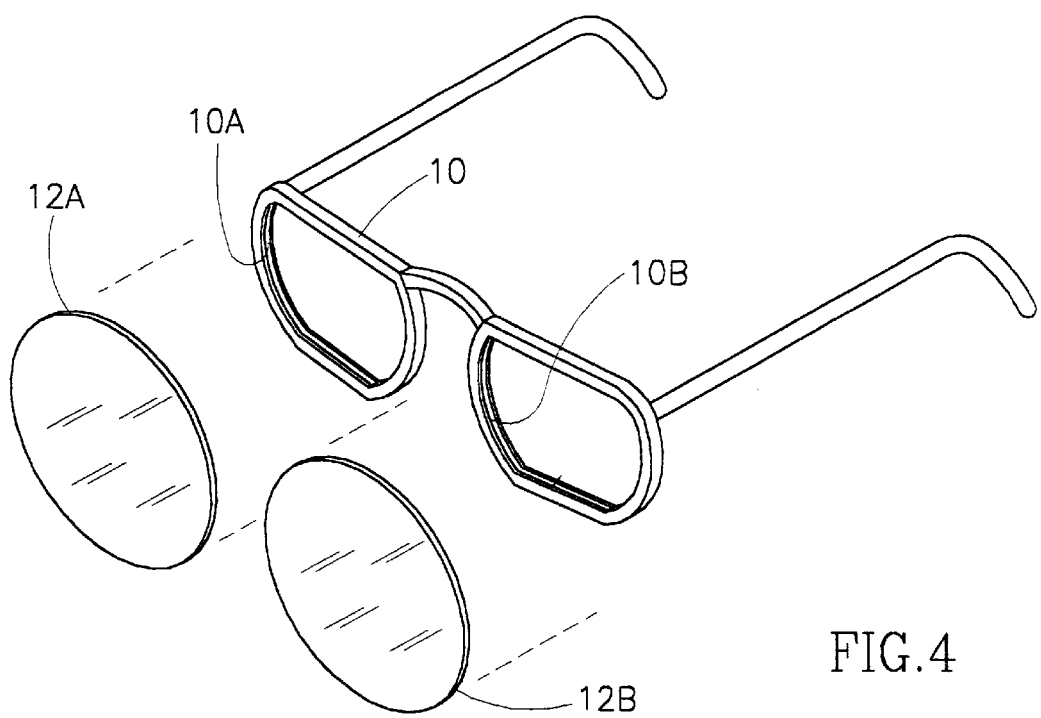
FIG. 4 is a pictorial illustration of the frame of a patient's spectacles and a pair of lenses to be mounted into the frame.

Referring to FIG. 4, there is illustrated a frame 10 and a pair of progressive lenses 12a and 12b to be mounted in the frame 10 so as to completely form a patient's spectacles. The frame 10 defines a pair of spaced inner contours 10a and 10b. The lenses 12a and 12b are manufactured in a conventional manner and are chosen in accordance with an "addition" defined by prescribed values of optical power for the patient's distance and reading vision and cylinder parameters (if any). As shown, the lenses 12a and 12b are of substantially circular contours, which should be cut so as to suit the contours 10a and 10b, respectively, of the frame 10.

Figure 5:
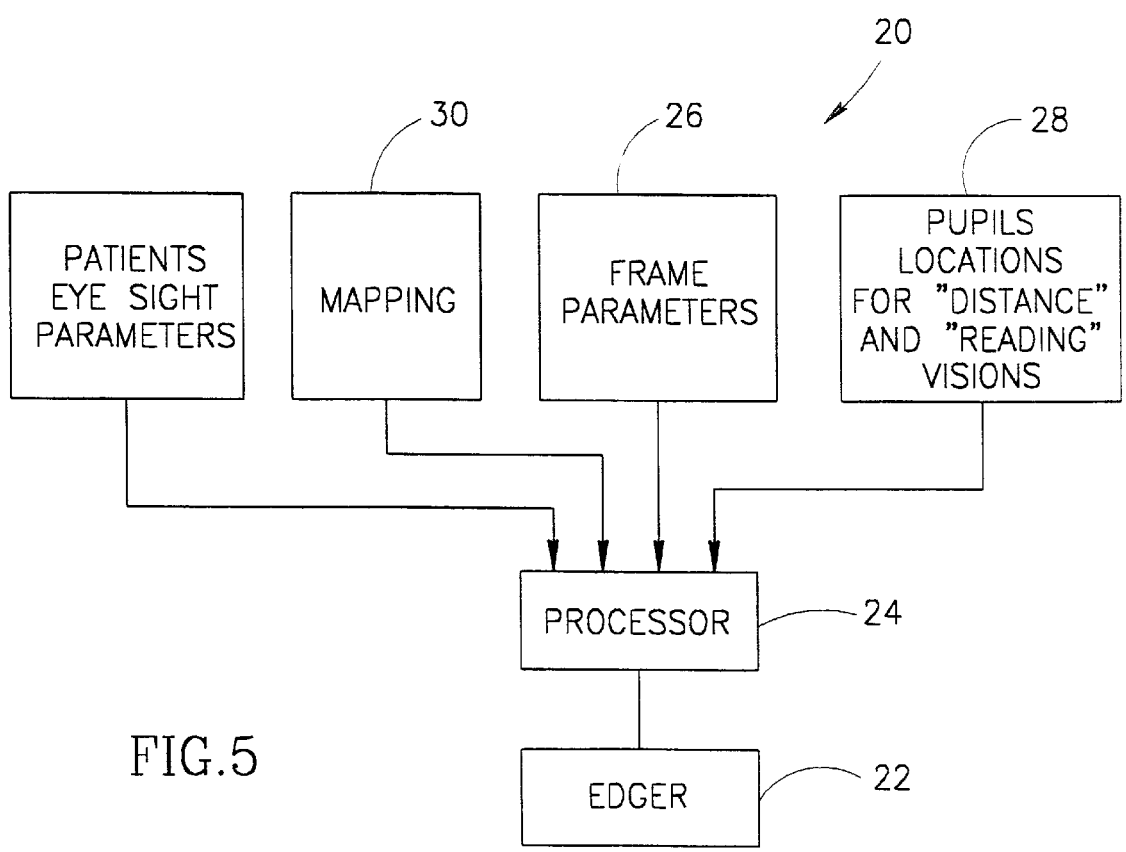
FIG. 5 is a block diagram showing the main components of a system according to the invention.

Turning now to FIG. 5, there is shown a system, generally designated 20, for adjusting the progressive lenses 12a and 12b for mounting into the frame 10. The system 20 comprises an edger 22 used for positioning and orienting each of the lenses 12a and 12b relative to the respective contours 19a and 10b, and for circumferentially cutting the lenses. The edger 22 is a known device, and its construction and operation do not form parts of the present invention.

The system 20 further comprises a processor 24 coupled to the edger 22 for operating the latter. The following information is input into the processor 24:

frame parameters;

patient's parameters, i.e., his pupils' locations relative to the frame for distance and natural reading visions; and lens parameters represented by lens maps such as shown in FIG. 2.

The frame parameters may be obtained by a measuring device 26. Alternatively, data representative of different frames parameters may be pre-stored in the processor 24. It is also possible, although not specifically shown, that the device 26 be a constructional part of the edger 22.

The pupils' locations for distance and natural reading visions are obtained by means of a measuring device 28, which determines pupils' locations of each patient's eye relative to the respective contour 10a or 10b of the frame 10 for both the distance and reading vision. The preferred embodiment of the construction and operation of the device 28 will be described further below with reference to FIGS. 8 and 9a–9d.

The lens parameters include power and distortion distribution in the lens, and the lens "addition" corresponding to prescribed values of the optical powers required for the patient's eyes for distance and reading vision, as described above with reference to FIG. 2. These parameters may be determined either by means of an appropriate mapping device 30 coupled to the processor 24 for reproducing a map for each of the lenses 12a and 12b such as, for example, so-called "Moire Deflectometer" produced by Rotlex Ltd, or from maps or the like data supplied by a manufacturer of the lenses 12a and 12b.

The main principles of operation of the system 20 will now be described with reference to FIG. 6. The optician receives the pair of lenses 12a and 12b from the manufacturer and the frame 10 from the patient. The optician operates the device 30 for determining the above parameters of each of the lenses and the device 26 for determining the frame parameters. Then, the optician operates the device 28 for determining the pupils' locations relative to the frame for distance and habitual reading visions. All the measured data is input into the processor 24 in a conventional manner. The processor 24 is operated by suitable software for analyzing the input data.

There is usually no problem to adjust the inter pupillary distance for distance vision so as to match the far vision zones 2 of both lenses 12a and 12b. Indeed, as clearly seen in FIG. 2, the zone 2 is always surrounded by a free of distortions region. As for the near vision zone 3, upon detecting by the processor 24 that the pupil location does not match the zone 3 of the either lens, the processor generates a decision accordingly for indicating to the optician how to orient the lens 12a or 12b relative to the respective contour 10a or 10b for obtaining the matching.

Figure 6:
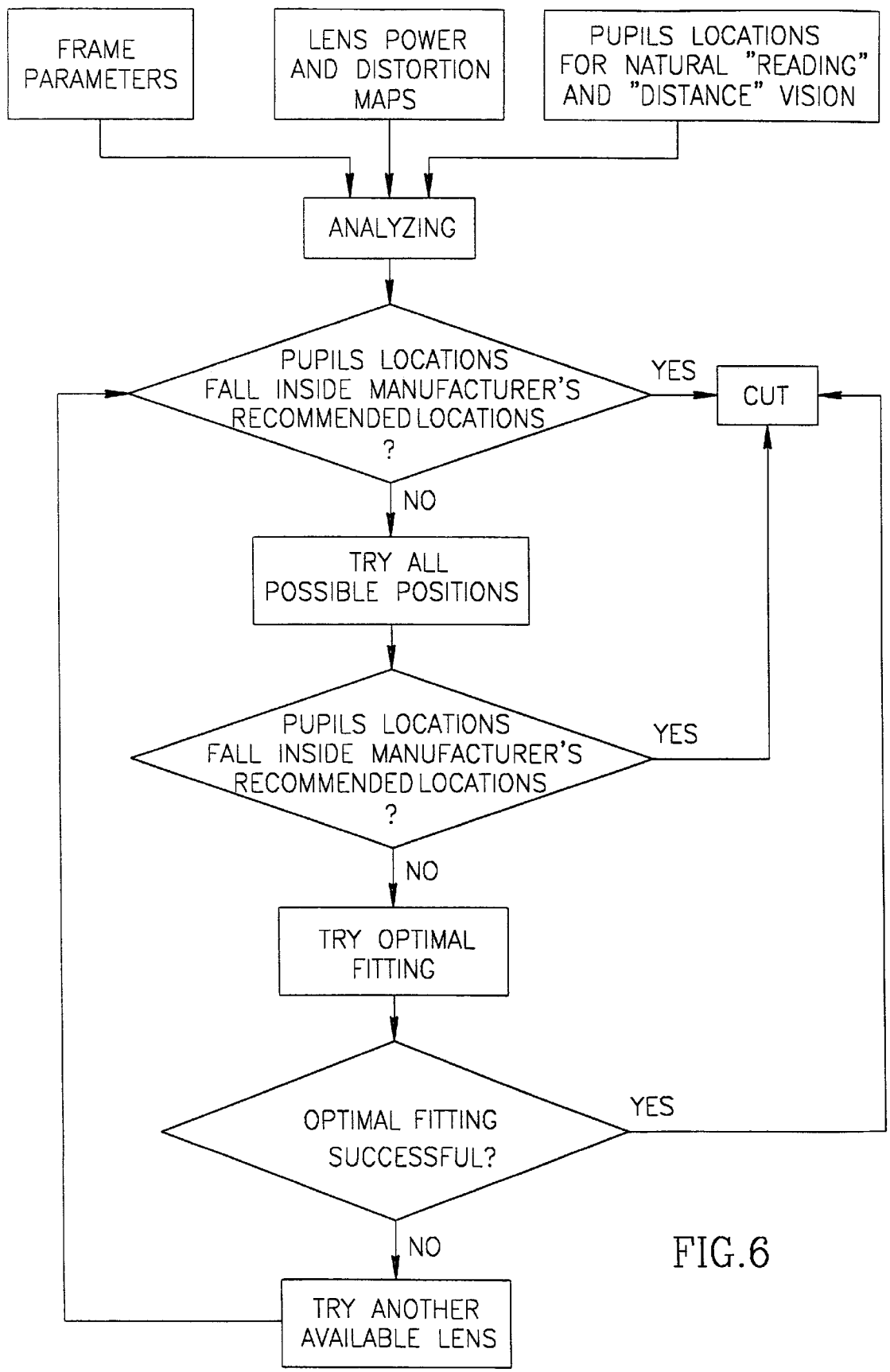
FIG. 6 is a flow diagram illustrating the principles of operation of the system of FIG. 5.

As shown in FIG. 6, in cases where a "YES" answer cannot be attained for the query: "PUPIL'S LOCATION FALL INSIDE MANUFACTURER'S RECOMMENDED LOCATIONS?", the process can still go on by tying all possible positions, optimal fitting and, if required selecting another lens. From the prior stage, where exact prescribed power and actual zero distortion was required (but was not fulfilled), the programmed processor started an optimization algorithm. The processor's task is to evaluate not only the lens' parameters (power and distortion) at the precise pupil location, but also those of the near and far neighborhood.

Figure 7:
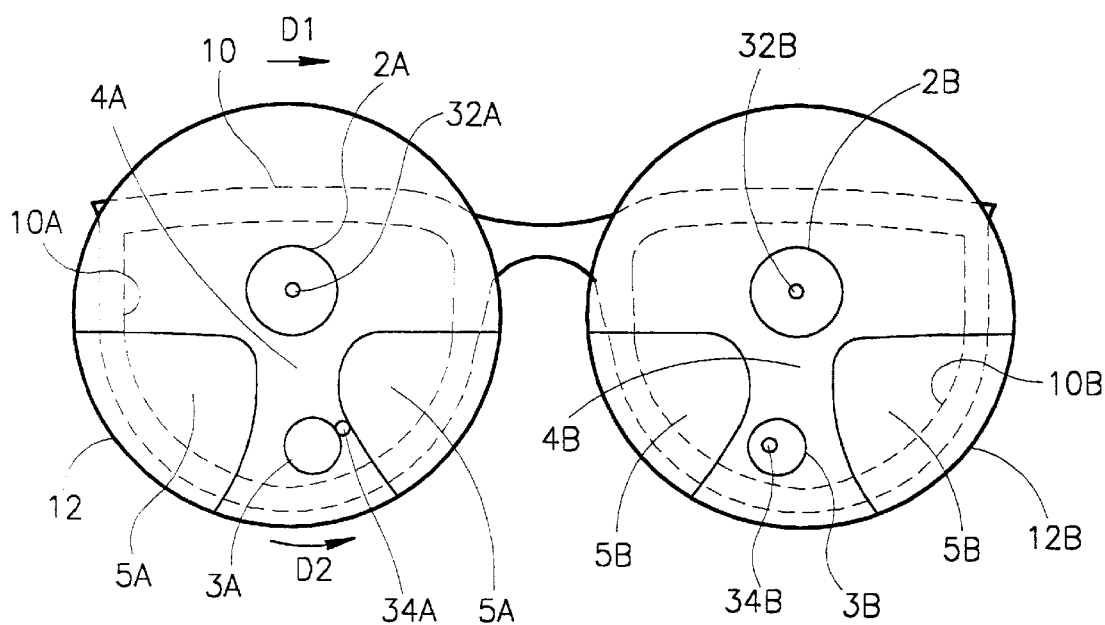
FIG. 7 more specifically illustrates the principles of operation of the system of FIG. 5 for adjusting the lens of FIG. 2 for mounting into the frame of the spectacles.

Reference is now made to FIG. 7 illustrating a process of making the above decision for one example of a possible adjustment. The lenses 12a and 12b are positioned opposite to the frame 10 so as to facilitate understanding regarding the locations of the zones 2a, 3a, 4a, 5a and 2b, 3b, 4b and 5b relative to the contours 10a and 10b, respectively. Small regions 32a and 32b correspond to pupils' locations relative to the contours 10a and 10b for distance visions of the patients eyes. As indicated above, the pupil location for distance or natural reading vision is the location of intersection of the patient's line of sight in, respectively, distance or natural reading mode, with the plane defined by the frame relative to the frame. In other words, lines of sight (not shown) of the patient's eyes intersect frame planes defined by the contours 10a and 10b in the regions 32a and 32b, which will be described in further details below. Similarly, small regions 34a and 34b correspond to pupils' locations relative to the frame for habitual reading vision. As clearly shown, the regions 32b and 34b fall within the zones 2b and 3b substantially at the center region between two opposite distortion zones 5b, and, therefore, the lens 12b satisfies the requirement of patient's left eye. As for the patient's right eye, the pupil location 34a falls close to a boundary region between the near vision zone 3a and the distortion zone 5a. It is appreciated that the patient would not feel comfortable with such spectacles. However, when observing the whole map of the lens 12a relative to the contour 10a, it becomes clear that either displacement of the lens 12a towards a center of the frame 10, i.e. in a direction $D_1$, or rotation of the lens 12a about an axis thereof in a direction $D_2$, would result in both regions 32a and 34a being in allowed locations. Regarding the rotation option, it will be mostly preferably over translation because it enables to keep the line connecting the zones 2a and 3a within the zone 4a of continuous focus. But in this case, the optician should change the parameters of a specific cylinder as prescribed by the optometrist by the amount of the expected rotation, when delivering this information to the lab before polishing the lens.

Alternatively, although not specifically shown, the case may be such that the pupil location for natural reading is vertically displaced from the typical position of the near vision zone of either lens. In such a situation, the pupil's location may, for example, fall within the zone of continuous focus at such a point on the lens where the optical power of the latter is less than that required for a patient for reading vision.

It is thus clear that although the pupil location 34a is well within a free distortion zone, the patient would still not feel comfortable because of the lack of "symmetry" around this location, i.e. the nasal vision field is appreciably more distorted than the temporal field. This is a clear example of the influence of far neighborhood. By using, for example, a method of weighing function, the processor can allocate a "weight" to this asymmetry and similar asymmetries, like in the far sight pupil location, and add up to the total weight. A weight algorithm is an example of a way to reach straightforwardly optimal matching of several parameters, even if absolute matching between the pupils and the lens' markings has not been achieved The most important teaching of the present invention is that even when there is no way of fitting the lens to the pupil location according to the lens' markings (or equivalent data), there is still a way to achieve optimal fitting. Utilizing the lens' maps through the optimizing process, the only limiting conditions for the power and distortion are: (a) the power is substantially of the prescribed value according to predefined tolerances; and (b) the distortions are minimal according to predefined tolerances.

The conventional approach for providing the patient's spectacles is based on the fact that a lens "addition" is determined by an optometrist, and the near vision zone 3 is located at a certain standard position in the lens. It is thus appreciated that, for example, in case where the pupil's location for reading falls "higher" than the standard location 8, than the optician, who is provided inter alia with the measuring device 28 and reference data representative of a plurality of maps of standard lenses manufactured by various producers, may prescribed a lens of an "addition" higher than that defined for the patient. This would have resulted in the pupil location for reading vision falling within that zone of the lens, which has the required power value and is still free of distortions. Of course, in this case the latitudinal symmetry may be reduced, and it is apt to the processor to evaluate this option. Thus, the provision of the device 28 and, additionally, a reference data presenting various maps of standard lenses, enables the optometrist to choose the most suitable lens' parameters, i.e. the optical power and distortions distribution, for meeting the requirements of the patient's eyesight and the frame parameters, i.e. pupils' locations relative to the frame for distance and reading visions. In other words, the optometrist may choose the most suitable progressive lenses to make an order.

Figure 8:
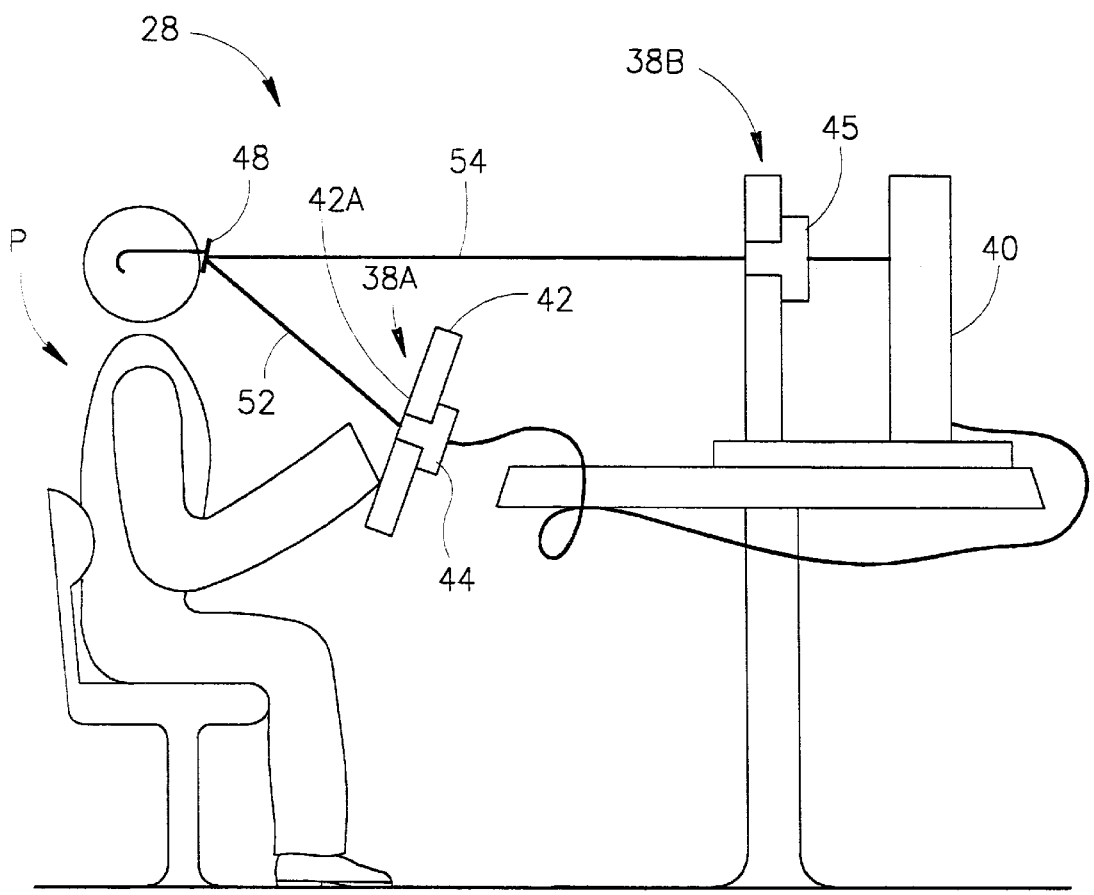
FIG. 8 is a schematic illustration of a measuring device of the system of FIG. 5.

Reference is now made to FIG. 8, illustrating the main components of the measuring device 28 for measuring the patient's pupil's locations in his habitual reading and distance mode. The device 28 comprises first and second reading units designated generally as 38a and 38b, respectively, and an image processor 40. The reading unit 38a includes a support target member 42 in the form of a lightweight movable box sized like a common book. A front outer surface 42a of the member 42 has reading material mounted thereon (not shown here), e.g., a part of newspaper, two book pages or the like. Generally speaking, the font's size of the reading material should be the same as that found in a common book. The units 38a and 38b include conventional CCD cameras 44 and 45, respectively, whose output circuits are coupled to the image processor 40, either through wires or wireless (e.g., by radio or infrared transmission) in a conventional manner.

Figure 9A:
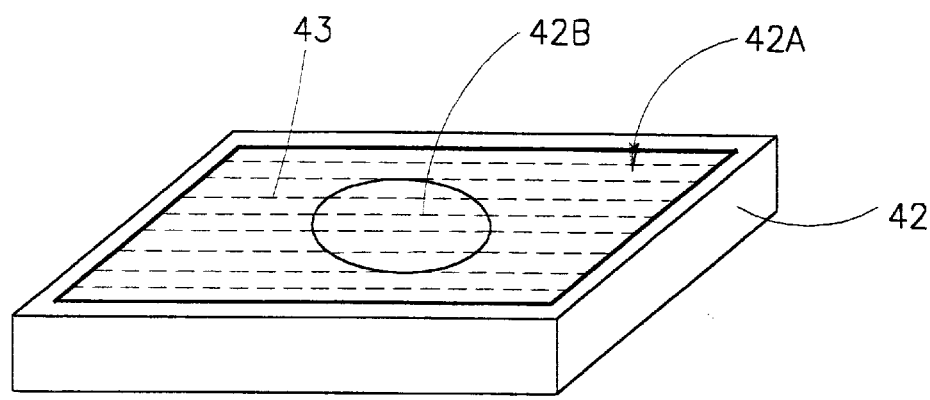
FIGS. 9a–9d more specifically illustrate the constructional and operational principles of the measuring device of FIG. 8.
Figure 9B:
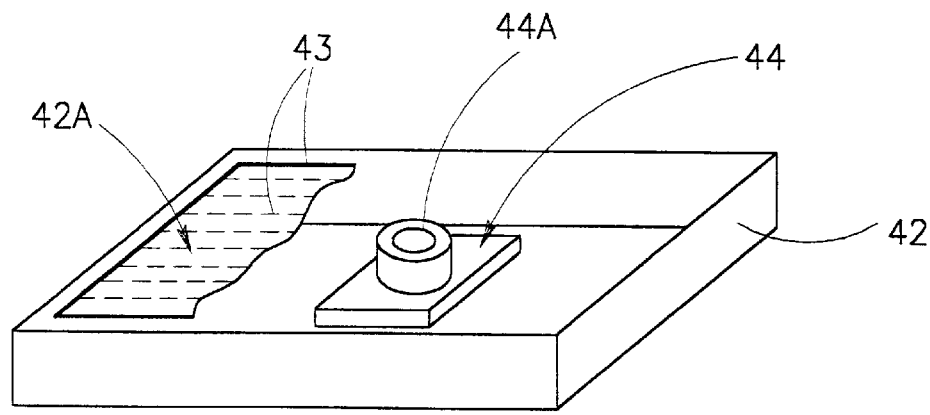

As more specifically illustrated in FIGS. 9a and 9b, the construction may be such that the front panel 42a is formed with a transparent or semi-transparent (half-mirror) window 42b, with the reading material 43 on it. In this case, the corresponding CCD camera is located inside the box member 42. This camera may be accommodated opposite the window 42b, or at any other location inside the member 42, provided a suitable light directing means are accommodated inside the member 42 between the window and the camera for receiving and directing light towards the camera.

Figure 9C:
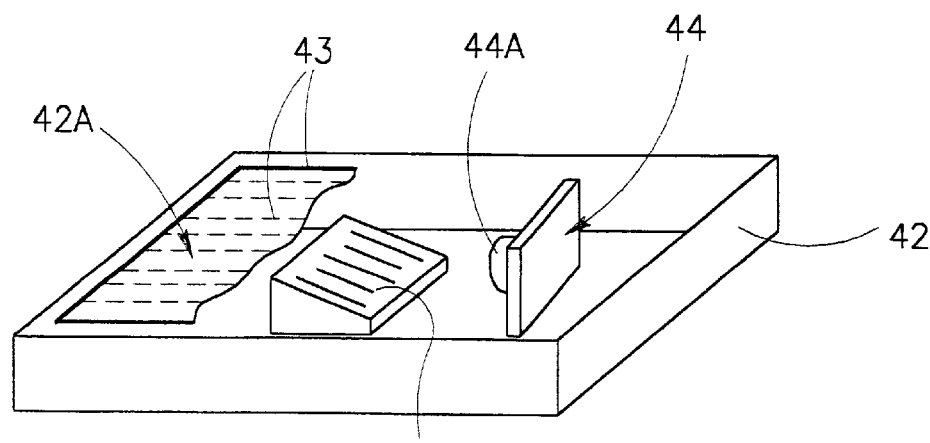

In the example of FIG. 9b, the camera 44 is oriented such that its sensing surface 44a is substantially parallel to the surface 42a. FIG. 9c shows an example, where the sensing surface of the camera is substantially perpendicular to the surface 42a. In this case, a mirror 46 is appropriately mounted to reflect light towards the camera 44. The orientation of the camera is dictated by its dimensions so as to enable the entire member 42 to be of the desired size. It should be noted, although not specifically shown, that the construction may be such that a mini-camera is accommodated on the surface 42a between the lines of the reading material 43.

Thus, the camera 44, while being obscured from the patients, is able to take pictures of the patient's eyes and specifically his pupils' locations relative to the frame, and to transfer data indicative thereof to the processor 40.

Turning back to FIG. 8, a patient, P, sits in front of a table, puts on a frame 48 and starts to read the printed data holding the support member 42 in the most convenient position for him to read. The CCD camera 44 is preset so as to have the patient's eyes located within the depth of field of the camera. As for the reading material, it is at such proximity of the CCD camera 44, that it never falls within its depth of field. Therefore, the CCD camera 44 is adapted to capture real pictures of the patient's eyes disposed within the contours of the frame 48 during the real process of reading. Actually, such picture presents the patient's pupils locations relative to the frame.

It should be noted, that the case may be such that a patient is used to read with a book lying on the table. In this case, the camera located inside the member 42 may not "see" his eyes when reading. To enable the capture of the picture of the patient's eyes at his natural reading position, the window 42b should be in the form of a semi-transparent mirror, and the reading material or any other geometrical pattern should be printed or painted on the outer surface of the window. The patient, after achieving his habitual posture, will be asked to turn the device without changing his position until the image of his eyes is reflected back in the half-mirror window. This simple procedure can save installation of a complicated camera tracing system. The printed or painted letters on the window will not interfere with the patient's image on the camera focal plane, since they are too close to the camera's objective lens and, therefore, are out of the camera's depth of field.

It should also be noted that some patients need high power, corrective lenses for reading. In this case, the patient would not be able to read with a clear frame, namely would not be able to demonstrate his natural reading position. To this end, instead of measuring the absolute pupils' location for reading with the selected clear frame, the pupils' locations for reading and distance vision will be measured while the patient wears his single-vision reading glasses in both measurements. Then, the selected clear frame will be put on and the pupils' locations for distance vision only will be determined. Based on the relative position of the pupils locations for reading vision relative to those for distance vision as measured with the single-vision reading glasses, the pupils' locations for reading vision for the selected frame will readily be calculated. Evidently, a trial frame with appropriate corrective lenses can be used instead of reading glasses. Although a certain inaccuracy is induced with this procedure, this inaccuracy can be reduced to fairly low value with simple mathematical calculations.

Thus, the pupils' images are transferred from the camera 44 to the image processor 40, were they are analyzed to calculate the relative pupils' locations relative to the spectacles frame. Since the fame sizes are known, or, alternatively, a standard object of known sizes may be mounted on or stuck to the frame, a transforming scale function can be created to calculate the frame's tilting angle in the vertical plane, as well as the turning angle of the patient's head in the horizontal plane. These angles are needed to correctly transform back the distorted frame's image in reading mode caused by the relative angles between the camera axis and the normal to the frame's plane.

The pupils' locations for far sight or their relative positions to the reading locations are also needed for the optimal fitting. In the present example of FIG. 8, these measurements are performed with the unit 38b. But, actually, this may be carried out with the same unit 38a. In this case the box member 42 is remounted in front of the patient at his eyes' level, and the patient, instead of focusing his eyes on the reading material, will be asked to fix his eyes at far object. Additionally, the camera support for far vision will be preferably mounted on a vertical translating stage (not shown) to allow for different patient body height.

Figure 9D:
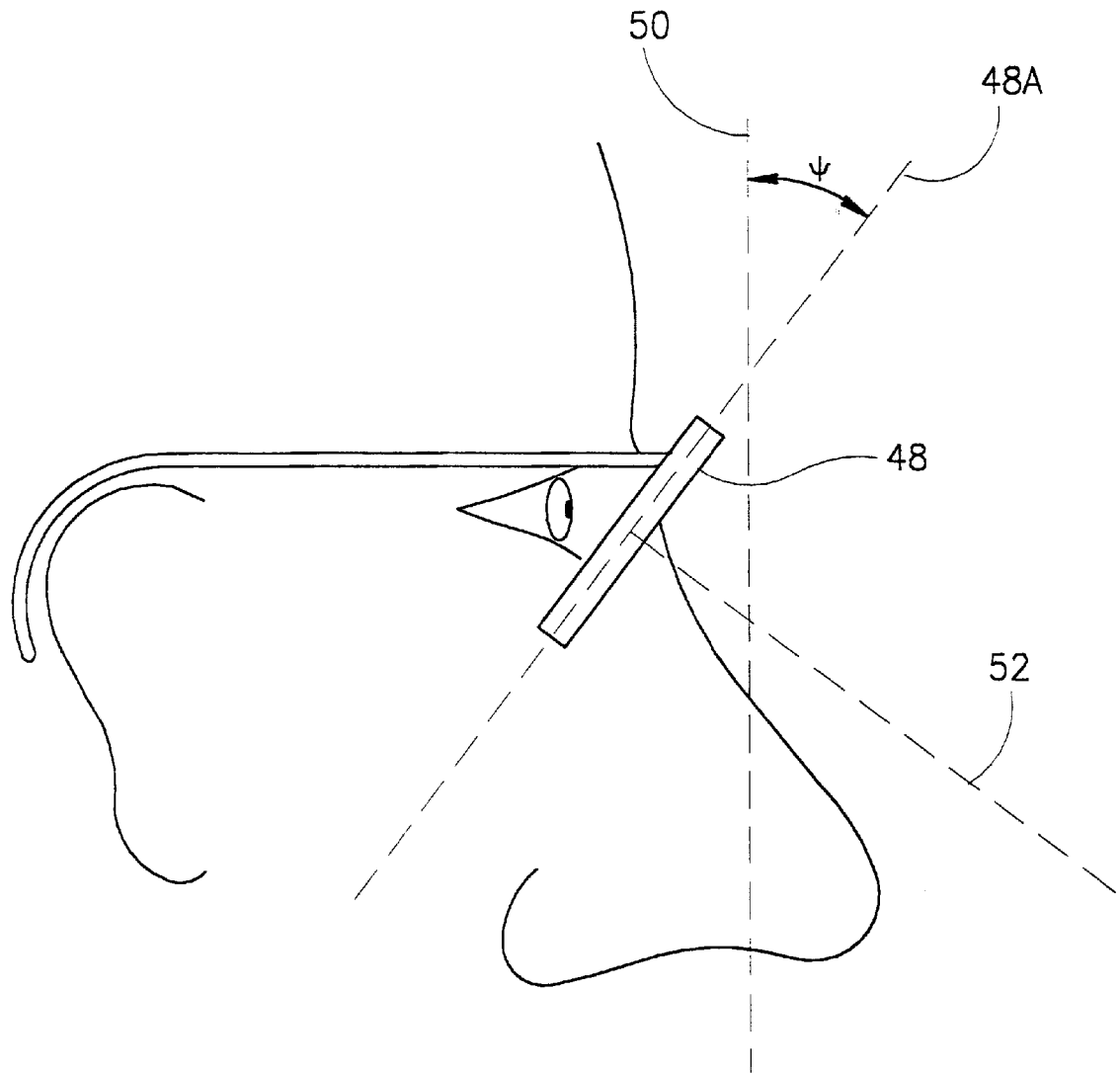

The optician has optional, added capabilities to check and/or measure physical parameters that relate to the compatibility of the frame to the patient's face. As shown in FIG. 9d, the frame 48 defines a plane 48a, which is not parallel to a plane 50 defined by the patient's face. The plane 48a is always inclined forward, i.e., away from the face plane 50 at a certain angle V (the pantoscopic angle). The angle $\psi$ depends on the profile of the patient's face. The more the angle $\psi$, the more the probability that a line 52 of sight for reading vision, as well as a line of sight 54 for distance vision (FIG. 8) would not cross the frame's plane 48a within the zones 2 and 3 of the lens. This results in that, even when prescribing correct parameters of the lenses according to the patient's eyesight and pupils' locations, the final mounting of lenses in the frame would not be successful. To this end, by rotating the patient's seat by 90° and taking the patient's side view picture, the pantoscopic angle $\psi$ or the frame's plane distance from the cornea can be measured.

It is readily appreciated that various modifications can be applied to the above embodiments, provided the following conditions are satisfied in order to measure the habitual reading pupil locations:

an actual readable and meaningful reading material is placed on the front panel of the reading unit;

the weight and the size of the reading unit do not exceed those of a common book;

the seat and the optionally provided table in front are aligned to the patient's most convenient position in order to simulate his habitual reading posture;

the patient is allowed to put the reading unit on the table in front of him, if he uses to read in that way;

the reading material is well illuminated, preferably with ambient light (the background noise level being kept low);

lighting of the patient eyes with a blinding light (includes flashlights) is avoided;

preferably, the patient is not aware of being watched by cameras (cameras are covered by half-mirror windows).

It thus becomes clear that such parameters about a specific patient as his pupils locations relative to the frame for each eye at his natural reading position are very important and should, therefore, be considered at the first stage of prescribing the lens parameters by an optometrist, and at the last stage of adjusting the lens for mounting into the frame. Additionally, these data in combination with such parameters of lenses prescribed to the specific patient as the power and distortion distribution should be analyzed so as to determine whether the optimal positioning of each of the lenses relative to frame can be achieved, according to predefined tolerances, and, if not, to select a correct lens to replace the prescribed one.

Those skilled in the art will readily appreciate that various modifications and changes may be applied to the above-described embodiments of the invention without departing from its scope defined in and by the appended claims.

What is claimed is:

1. A device for determining patient's pupils locations for natural reading mode, the device comprising:

(a) a target member with a reading material on its outer surface, wherein said target member is orientable by the patient in a manner corresponding to his natural reading position; and (b) a video camera mounted within said target member and disposed such that the patient's eyes are located within the depth of field of the camera, the camera thereby acquiring an image of the patients' eyes in a frame of his spectacles, whilst the patient reads said reading material in his natural reading position, enabling to determine an intersection of a line of sight of each patient's eye with a plane defined by the frame relative to the frame.

2. The device according to claim 1, wherein said outer surface is formed with a window, said camera being located inside said target member so as to acquire the image through said window.

3. The device according to claim 2, wherein said window is a semitransparent mirror.

4. The device according to claim 2, wherein said window is formed with a pattern on its outer surface.

5. The device according to claim 4, wherein said pattern is a reading material.

6. The device according to claim 1, wherein said camera is mounted on said outer surface between adjacent lines of the reading material.

7. The device according to claim 1, wherein said target member is a box sized like a common book, font's size of the reading material being as of a common book.

8. The device according to claim 1, wherein said target member is displaceable to be mounted in front of the patient at his eyes' level, said camera being thereby adapted to acquire an image of the patients eyes in the frame, when disposed for distance vision.

9. A method for adjusting a progressive lens relative to the frame of a patient's spectacles, wherein the lens has power and distortion distributions defining far and near vision zones which are located in accordance with prescribed first and second values of the optical power required for the patients eye at its distance and reading modes, respectively, and are spaced from each other by a zone of continuously variable power, the method comprising the steps of:

(i) determining a location of intersection of a line of sight of the patient's eye at reading mode with a plane defined by the frame of the spectacles relative to said frame, wherein said determination is performed at the patient's natural reading position by using a device comprising:
   a target member having a reading material on its outer surface, wherein said target member is orientable by the patient in a manner corresponding to his natural reading position; and
   a video camera mounted within said target member and disposed such that the patient's eyes are located within the depth of field of the camera, the camera thereby acquiring an image of the patients' eyes in a frame of his spectacles, whilst the patient reads said reading material in his natural reading position, enabling to determine the intersection of the line of sight of each patient's eye with the plane defined by the frame relative to the frame;

(ii) determining the distributions of said optical power and optical distortions of the progressive lens;

(iii) analyzing data indicative of the determined location of intersection of the line of sight of the patient's eye at said natural reading mode with the plane defined by the frame of the spectacles relative to said frame, and data indicative of the determined distributions of said optical power and optical distortions of the progressive lens, for determining whether an optimal positioning of the lens via at least one of a horizontal translation, a vertical translation, and a rotation of the lens relative to said frame can be achieved;

(iv) if said optimal positioning of the lens cannot be achieved, replacing the prescribed lens by another lens having at least one different parameter as compared to that of said prescribed lens; and (v) if said optimal positioning of the prescribed lens can be achieved, generating data representative thereof and using said generated data for mounting the lens into the frame.

10. The method according to claim 9, wherein said optimal positioning of the lens is aimed at providing such a relative position of the lens mounted in the frame at which the line of sight corresponding to the natural reading mode passes through the lens at a location thereon, in which the optical powers of the progressive lens is substantially of the prescribed value and the optical distortions are minimal and the pupil location for natural reading fulfills predefined tolerances relating to the power and distortion of the close and far neighborhoods of this location.

11. The method according to claim 9, wherein said analyzing is carried out by a programmable means.

12. The method according to claim 9, and also comprising the steps of:
   determining a location of intersection of a line of sight of the patient's eye at a distance mode with the plane defined by the frame of the spectacles relative to said frame;
   analyzing data indicative of the determined location of intersection of the line of sight of the patient's eye at said distance mode with the plane defined by the frame of the spectacles relative to said frame, said optimal positioning of the lens being aimed at providing such a relative position of the lens mounted in the frame at which the lines of sight corresponding to the distance and natural reading modes pass through the lens at locations thereon, in which the optical powers of the progressive lens are substantially of the first and second values, respectively, and the optical distortions are minimal and pupils locations are fulfilling predefined tolerances relating to the power and distortion of the close and far neighborhoods of these locations.

13. The method according to claim 9, wherein the determination of the power and distortions distributions comprises processing the lens in a "mapping" system.

14. The method according to claim 9, wherein the determination of the power and distortions distributions comprises analyzing reference data representative of a plurality of maps of standard semi finished lenses manufactured by various producers.

15. The method according to claim 9, wherein said optimal positioning of the lens for mounting it in the frame is performed on an edger device in which there are provided linear and rotational movements of the lens.

16. A system for adjusting a progressive lens relative to a frame of a patient's spectacles, wherein the lens has distributions of the optical power and optical distortions therein defining far and near vision zones which are in accordance with prescribed first and second values of the optical power required for the patient's eye at its distance and reading modes, respectively, and are spaced from each other by a zone of continuously variable power, the system comprising:
   a device for determination of a location of intersection of a line of sight of the patients eye for said natural reading mode with a plane defined by the frame of the spectacles relative to said frame, wherein said device comprises:
      a target member having a reading material on its outer surface, wherein said target member is orientable by the patient in a manner corresponding to his natural reading position; and
      a video camera mounted within said target member and disposed such that the patient's eyes are located within the depth of field of the camera, the camera thereby acquiring an image of the patients' eyes in a frame of his spectacles, whilst the patient reads said reading material in his natural reading position, enabling to determine the intersection of the line of sight of each patient's eye with the plane defined by the frame relative to the frame a device for determination of the distributions of said optical power and said optical distortions of said progressive lens;

a processor capable of analyzing data indicative of the determined location of intersection of the line of sight of the patient's eye at said natural reading mode with the plane defined by the frame of the spectacles relative to said frame, and data indicative of the determined distributions of said optical power and optical distortions of the progressive lens, and generating data indicative of an optimal positioning of the lens relative to said frame; and a device for positioning said progressive lens via at least one of a horizontal translation, a vertical translation, and a rotation relative to said frame for mounting the lens into the frame at said optimal position of the lens.

17. The system according to claim 16, wherein said optimal positioning of the lens is aimed at providing such a-relative position of the lens mounted in the frame at which the line of sight corresponding to the natural reading mode passes through the lens at a location thereon, in which the optical power of the progressive lens is substantially of the second value and the optical distortions are minimal and at which pupil location for natural reading mode fulfills pre-defined tolerances relating to the power and distortion of the close and far neighborhoods of this location.

18. The system according to claim 16, and also comprising a device for determination of a location of intersection of a line of sight of the patient's eye for said distance mode with a plane defined by the frame of the spectacles relative to said frame, said processor being capable of analyzing data indicative of the determined location of intersection of the line of sight of the patient's eye at said distance mode with the plane defined by the frame of the spectacles relative to said frame.

19. The system according to claim 16, wherein said device for determining the distributions of said optical power and said optical distortions of said progressive lens comprises a mapping system for acquiring and processing power and distortion images of the lens.

20. The system according to claim 16, wherein said device for determining the distributions of said optical power and said optical distortions of said lens comprises a memory for storing reference data representative of a plurality of maps of standard semi finished lenses manufactured by various producers.

21. The system according to claim 16, wherein said device for positioning of said progressive lens comprises an edger device enabling linear and rotational movements of said progressive lens.

* * * * *